United States Patent
Pankratz et al.

(10) Patent No.: US 7,205,158 B2
(45) Date of Patent: Apr. 17, 2007

(54) METHOD FOR ASPIRATION OF A LIQUID SAMPLE

(75) Inventors: Thomas John Robert Pankratz, Newark, DE (US); William Jackson Devlin, Sr., Lincoln University, PA (US); David Russell Thompson, Kennett Square, PA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/871,409

(22) Filed: Jun. 18, 2004

(65) Prior Publication Data

US 2005/0282291 A1    Dec. 22, 2005

(51) Int. Cl.
   *G01N 1/10* (2006.01)
   *B01L 3/02* (2006.01)
(52) U.S. Cl. .............. 436/180; 436/174; 422/100
(58) Field of Classification Search ........... 422/100, 422/102; 436/174, 100, 180; 73/427, 864, 73/863.32, 864.01
   See application file for complete search history.

(56) References Cited

U.S. PATENT DOCUMENTS

| | | | | |
|---|---|---|---|---|
| 3,850,174 A * | 11/1974 | Ayres | ................ | 604/415 |
| 4,591,568 A * | 5/1986 | Banno et al. | ................ | 436/180 |
| 4,595,562 A * | 6/1986 | Liston et al. | ................ | 422/65 |
| 4,610,171 A * | 9/1986 | Nason | ................ | 73/864.62 |
| 4,824,560 A * | 4/1989 | Alspector | ................ | 209/208 |
| 4,853,137 A * | 8/1989 | Ersson | ................ | 210/782 |
| 5,019,349 A * | 5/1991 | Suzuki | ................ | 422/73 |
| 5,037,549 A * | 8/1991 | Ballies | ................ | 210/515 |
| 5,132,232 A * | 7/1992 | Parker | ................ | 436/177 |
| 5,474,687 A * | 12/1995 | Van Vlasselaer | ................ | 210/782 |
| 5,499,545 A | 3/1996 | Kimura et al. | ................ | 73/864.18 |
| 5,858,789 A * | 1/1999 | Francis et al. | ................ | 436/10 |
| 6,063,635 A * | 5/2000 | Ohta et al. | ................ | 436/54 |
| 6,100,094 A * | 8/2000 | Tajima | ................ | 436/54 |
| 6,220,075 B1 * | 4/2001 | Papen et al. | ................ | 73/1.74 |
| 6,322,752 B1 | 11/2001 | Siddiqui et al. | ................ | 422/100 |
| 2003/0099573 A1 * | 5/2003 | Tseung et al. | ................ | 422/63 |
| 2005/0095723 A1 * | 5/2005 | DiTrolio et al. | ................ | 436/180 |
| 2005/0124073 A1 * | 6/2005 | Freund | ................ | 436/177 |

* cited by examiner

*Primary Examiner*—Brian R. Gordon
(74) *Attorney, Agent, or Firm*—Leland K. Jordan (57) ABSTRACT

A liquid aspiration method which includes aspirating partial aliquots of liquid at a number of different depths of penetration of a pipette tip into a liquid. The different depths are selected so that partial aliquot segments are obtained throughout the entire depth of sample, optionally excluding the extreme top and bottom levels.

8 Claims, 5 Drawing Sheets

METHOD FOR ASPIRATION OF A LIQUID SAMPLE

FIELD OF THE INVENTION

The present invention relates to the transfer of an amount of liquid from one container to another, and more particularly, to a method for aspiration of whole blood from a sample tube using a vacuum actuated pipette.

BACKGROUND OF THE INVENTION

Clinical analyzers that automatically perform chemical assays and immunoassays of biological fluids such as urine, blood serum, plasma, cerebrospinal liquids and the like are in widespread commercial use. Generally, chemical reactions between an analyte in a patient sample and reagents used during analysis generate some sort of signal that can be measured by the analyzer. The concentration of analyte in the patient sample may be determined from this signal.

Clinical analyzers generally use aspirating means such as a hollow sampling probe or needle to transfer predetermined volumes of liquid samples or liquid reagents between receptacles, such as between sample containers, reagent containers and reaction cuvettes disposed on the analyzer. The aspirating means typically includes an elongated, needle-like pipette member having a hollow passage whereby liquid may be aspirated into and/or dispensed from the sample probe. The pipette is carried by a transport mechanism conventionally adapted to provide horizontal and vertical movement enabling the pipette tip to be lowered into a liquid for aspiration of the liquid, and for transporting the liquid to a site whereat the pipette is lowered to an optimal position for dispensing the liquid into another container. Some type of aspirating means, such as a piston and/or vacuum assembly, is controlled to aspirate liquid into the pipette and to dispense liquid from the pipette. Hereinafter, variations of the term aspirate refer to all of such processes for extracting liquid from one container and depositing at least some of the liquid into the same or another container and further includes the supporting devices required to complete the liquid handling operations.

U.S. Pat. No. 4,794,085 describes a method which permits the detection of penetration of liquid by an apertured container used for aspirating and dispensing the liquid. The apparatus has control means for advancing the container an increment of the maximum possible distance to the liquid, means to generate a pressure differential within the dispensing container that is sufficient to generate a signal that is indicative of whether the container aperture is closed by the liquid, and devices to detect and signal the pressure produced within the container by such a pressure differential.

U.S. Pat. No. 4,926,701 describes a pipetting device comprising a probe for dipping into a reservoir, reaction vessel or the like, a metering pump connected to the probe and a shutoff valve disposed between the probe and the pump are provided. In the intake phase of the pump with the valve open, first air and then a predetermined quantity of liquid is taken in.

U.S. Pat. No. 4,951,512 provides for providing access to a sealed container which temporarily provides an opening in the closures of the containers, and either removes contents, senses properties of the contents, or dispenses material into the container. A lift assembly moves each sample container upward against a puncture tube to produce an opening in the closure of the container. The system takes a sample through this opening or inserts a probe through the opening to measure the properties of the sample.

U.S. Pat. No. 5,163,582 covers an apparatus and method for dispensing a predetermined volume of liquid from a closed, liquid-containing blood collection tube. The apparatus includes a dual conduit providing a passageway for liquid to be dispensed from a closed blood collection tube and a gas conduit providing a passageway for gas to be introduced into the blood collection tube. Included in the apparatus is insertion of the dual conduit into the blood collection tube, turning the tube away from a vertical, upright orientation, connecting and disconnecting the gas passageway from a gas supply, displacing a volume of gas through the gas passageway, and controlling the operation of the apparatus.

U.S. Pat. No. 5,413,246 discloses a disposable apparatus to dispense an amount of liquid from a closed container using a stopper piercing means to access the interior of a closed blood collection tube, a gas passage means to allow a metered amount of gas to be forced into the blood collection tube, and a liquid passage means to allow fluid to be dispensed from the tube in proportion to the amount of gas forced into the tube.

U.S. Pat. No. 5,499,545 is a method for improving measurement accuracy by eliminating the influence of changes in the atmospheric and internal pressures on the quantity of a liquid absorbed or discharged. A pipetting device inducts a specified quantity of liquid into a tip portion or discharges a specified quantity of liquid from the tip portion by controlling the pressure inside a cylinder portion including a cylinder and a piston.

From the above art, it is evident that much attention has been given to extracting liquid samples from containers, without addressing another critical factor in obtaining accurate analytical measurements, that being aspiration of a uniform and representative aliquot portion of a patient sample from a sample container. This is an especially critical factor when the liquid to be analyzed is one of several body fluids as these frequently have a non-uniform composition. In particular, when the sample to be analyzed is a sample of whole blood that has not been preprocessed, a natural sedimentation occurs during a 30 minute period after the sample has been mixed, for instance by inversion of a primary whole blood tube. To compensate for such sedimentation, automated analyzers may be adapted with an automatic mixing mechanism, thereby adding complexity and cost as well as decreasing the reliability of an analyzer.

SUMMARY OF THE INVENTION

It is therefore an object of this invention to provide a method for aspirating a uniform aliquot of liquid into a pipette tip when the liquid has been at rest for a sufficient period of time so that sedimentation has occurred. This invention is accomplished by aspirating partial aliquots of liquid at a number of different depths of penetration of the pipette tip into the liquid. The different depths are selected so that equal-volume, partial aliquot segments are obtained throughout the entire depth of sample, optionally excluding the extreme top and bottom levels. In an alternate embodiment, the aspiration may be a continuous aspiration process between the uppermost and lowermost levels of fluid within the container. This invention then integrates the number of partial aliquot segments into a single full aliquot representative of a uniform sample, thereby avoiding the expense and complexity of an automatic mixing mechanism.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE PREFERRED EMBODIMENTS

Figure 1:
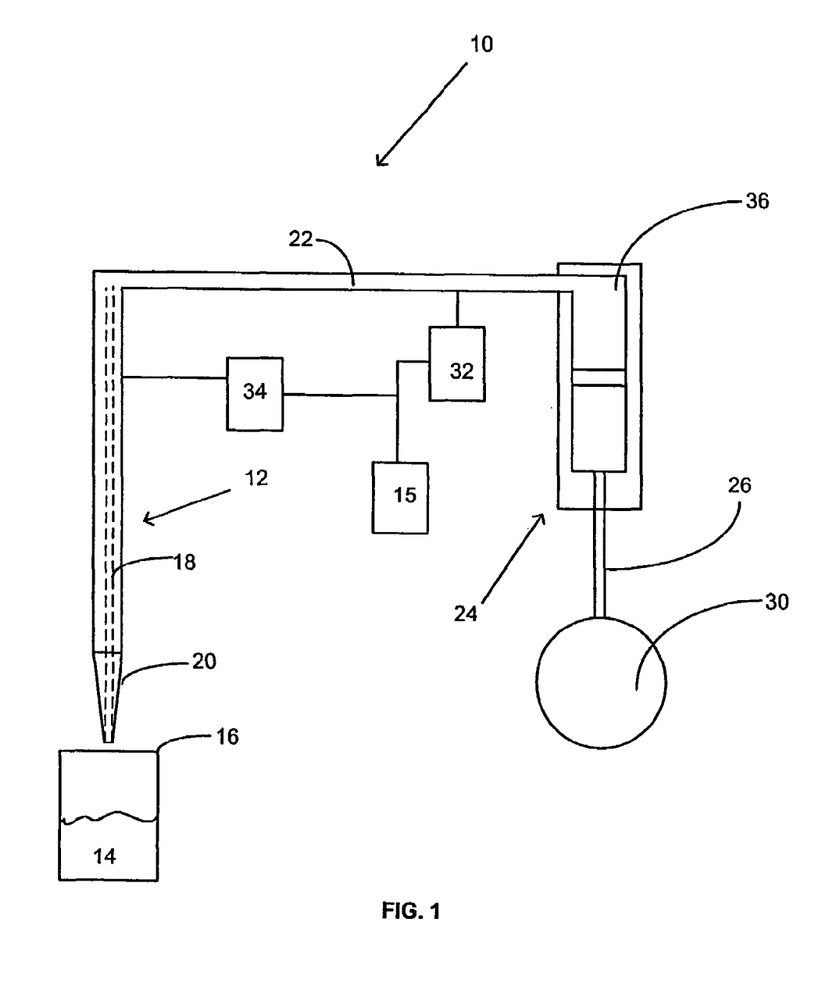
FIG. 1 is a schematic representation of an aspiration system in which the present invention may be practiced.

Referring to FIG. 1, there is illustrated a liquid aspiration system 10 according to the present invention which includes a pipette 12 for aspirating and dispensing liquid such as a sample liquid 14 contained in a sample tube 16. Although one such sample tube 16 is shown for the purpose of describing the liquid aspiration system 10, it will be apparent to those skilled in the art that any number of sample tubes 16 may be present. In an exemplary embodiment, the liquid aspiration system 10 would be used in an automated clinical analyzer (not shown). Such automated clinical analyzers are well known in the art and those skilled in the art know the functions of the elements of the analyzers to which reference is made.

Pipette 12 is of conventional design and typically has an elongate central hollow lumen 18, shown in dashed lines and extending lengthwise between a tip 20 and a vacuum line 22. Tip 20 may have a conically narrowing nose shape terminating in a distal orifice through which liquid is aspirated into lumen 18, and through which liquid is dispensed out from lumen 18. Liquid aspiration system 10 is typical of many such systems and comprises a piston assembly 24 in vacuum communication with pipette 12 via vacuum line 22. A piston 26 extends into a vacuum chamber 28 and is controlled by motor 30 to increase or decrease the vacuum pressure level within chamber 28, vacuum line 22 and lumen 18. A pressure transducer 32, typically placed in vacuum communication with vacuum line 22, monitors vacuum pressure within liquid aspiration system 10 and is conventionally employed as a feedback means operated in conjunction with motor 30 responsive to commands from a system computer 24 in order to precisely control vacuum pressure within lumen 18. Such devices and operations are well known in the art. Commercially available pipettors 12 made from metals like stainless steel or plastics like polypropylene and similar materials, and tubing 26 made from vinyl, polypropylene, polyethylene, metal, etc, may used in the present invention. Pressure transducer 32 measures air pressure within the pipette 12 both continuously and periodically during the aspiration method of the present invention. An exemplary pressure transducer 32 is Model SCXL004DN from SenSym, Miltipas, Calif., and is interfaced to computer 15 to provide a measured air pressure within tubing 22 and lumen 18.

Aspiration system 10 further comprises a transport mechanism 34 of conventional type adapted for moving pipette 12 laterally (X-direction), vertically (Z-direction) and from front to back (Y-direction) to move pipette 12 to an aspirating location above container 16, aspirate liquid 14 into lumen 18 from container 16, and to dispense a desired aliquot of sample liquid into an assay cuvette (not shown). Generally, a stepper-motor and limit-switches are used within transport mechanism 34 for transporting pipette 12 and these are interfaced to system computer 15 adapted and programmed to practice the present invention. Conventional electronic drivers and interface circuits are used to interface transport mechanism 34 and liquid aspiration system 10 to computer 15.

As mentioned previously, the present invention is directed at a method for overcoming the previous necessity to mix liquid having liquid susceptible to sedimentation in a sample container prior to aspiration. Table 1 shows settling rates for red blood cells in whole blood samples from various types of patients.

TABLE 1

| Patient | Red Blood Cell Settling Rate |
|---|---|
| Newborn Infant | 0–2 mm/hr |
| Young Children | 3–13 mm/hr |
| Post Adolescent Male | 1–15 mm/hr |
| Post Adolescent Female | 1–20 mm/hr |

In accordance with the present invention, pipette 12 is lowered into container 16 to ascertain the uppermost level of fluid 14. Various techniques are known in the art for such level determination, including capacitive, optical, and air pressure, and the choice is not critical in practicing this invention. Container 16 is supported so that the bottom of container 16 is at a known height, on an operating table for example, so that the overall total height or depth of liquid 14 may be determined by the difference between the uppermost level of fluid 14 and the known height of the bottom of container 16. According to one embodiment of this invention, seen in FIG. 2, the number of different aspiration levels at which a constant volume aspiration is effected may be determined from the height of the uppermost level of fluid 14 by assigning a constant difference between next adjacent aspiration levels. Alternately, as seen in FIG. 3, the number of aspiration levels at which a constant volume aspiration is effected may be predetermined, in which case the height of the uppermost level of fluid 14 may be used to determine the difference between next adjacent aspiration levels.

The present invention is practiced by operating transport mechanism 34 in conjunction with piston assembly 24 so as to aspirate a partial aliquot of sample liquid 14 at each of several next adjacent aspiration levels, the volume of each partial aliquot being controlled to provide a final aliquot of desired volume. In an illustrative embodiment, container 16 is a whole blood primary tube, for example of the EDTA type, and it has been predetermined to employ eight aspiration levels at which eight constant volume aspirations of partial aliquots of 25 uL blood each are effected at each of the eight next adjacent aspiration levels, providing a final aliquot of 200 uL. In an alternate embodiment, the aspiration may be a continuous aspiration process between the uppermost and lowermost levels of fluid within the container by continuously operating transport mechanism 34 in conjunction with piston assembly 24 so as to continuously lower pipettor 12 into sample liquid 14 and continuously operate piston assembly 24 so as to continuously aspirate liquid 14 between the uppermost and lowermost levels.

Figure 2:
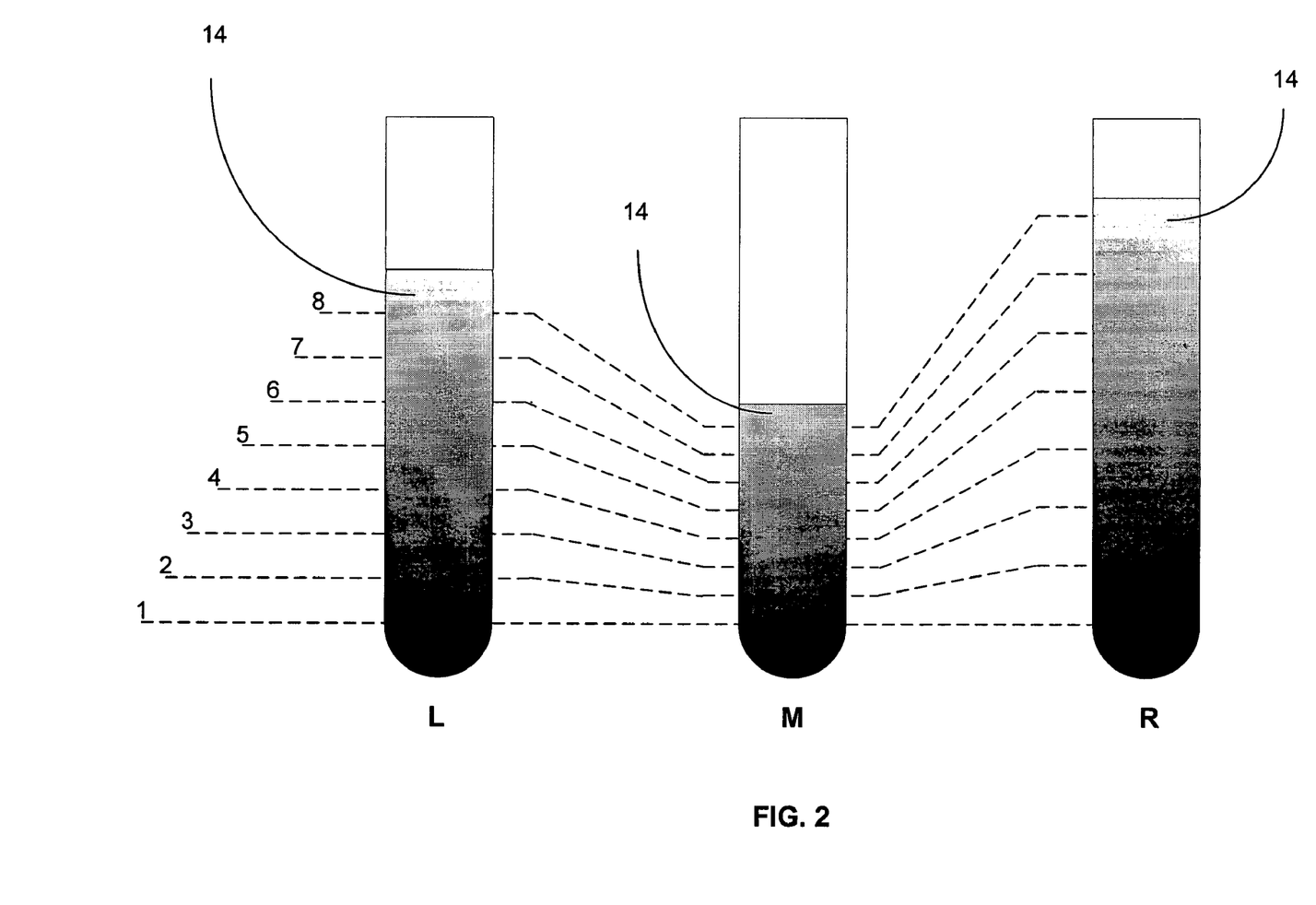
FIG. 2 is a graphical representation of one method of defining aspiration levels using the system of FIG. 1.
Figure 3:
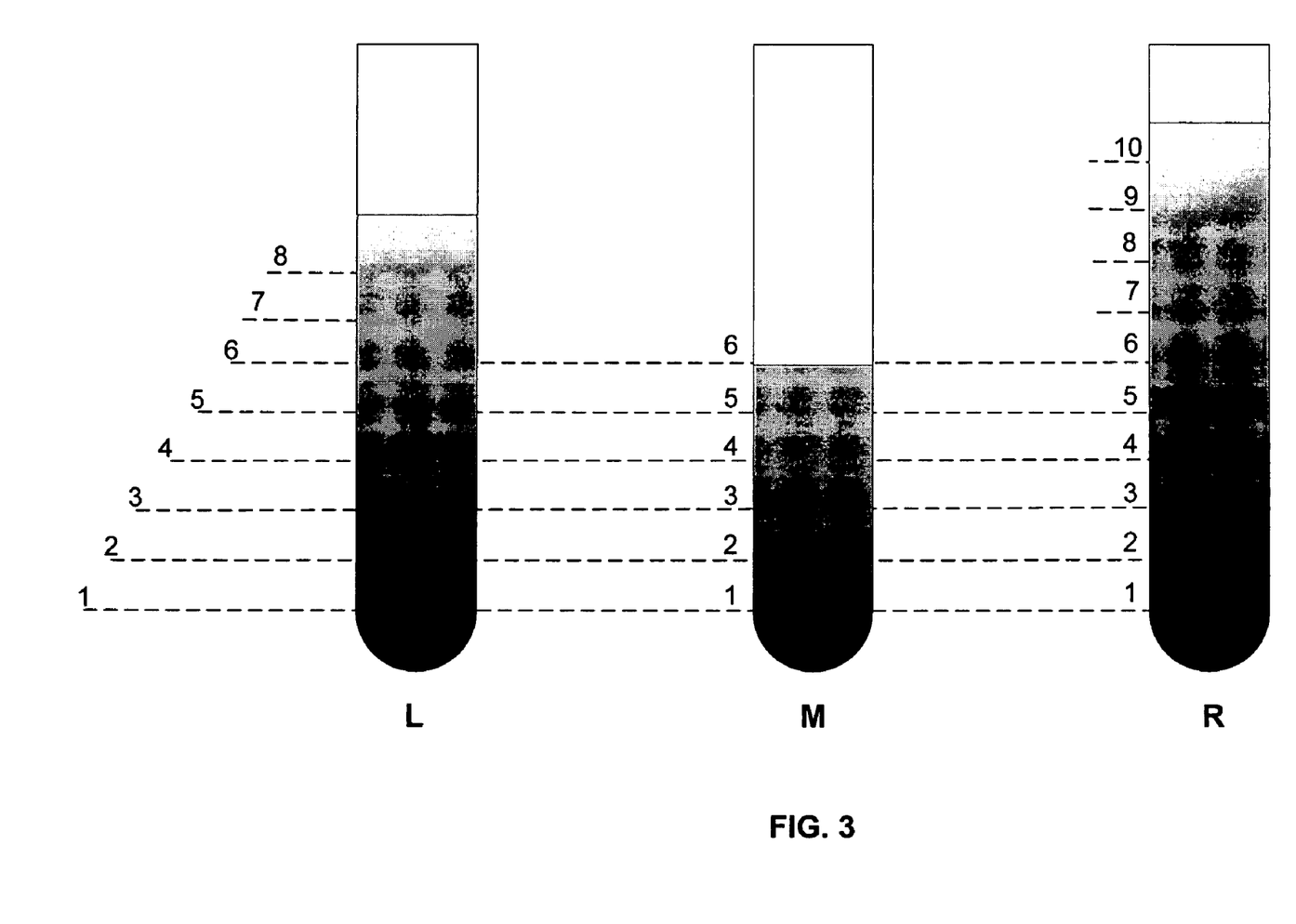
FIG. 3 is a graphical representation of an alternate method of defining aspiration levels using the system of FIG. 1.

FIG. 2 illustrates an exemplary embodiment of the present invention in an instance that three tubes contain different amounts of a liquid susceptible to sedimentation (the liquid is shaded more darkly at the bottom of the column of liquid than at the top) and it has been predetermined to employ eight aspiration levels at which eight constant volume aspirations of partial aliquots are effected. The numbered dashed lines indicate where aspiration of a partial aliquot of liquid is taken for eight different levels. The tube marked "L has a first amount of liquid therein and the eight different aspiration levels are a first distance apart; the tube marked "M" has a second volume which is less than the first amount of liquid therein, consequently the eight different aspiration levels are a smaller distance apart than the first distance; finally, the tube marked "R" has a third volume which is more than the first amount of liquid therein, consequently the eight different aspiration levels are a greater distance apart than the first distance. This illustration uses eight aspiration levels only as an example that is easy to illustrate in drawings. It must be appreciated by the reader that any number of aspiration levels, for example twenty, may be employed and remain within the bounds of the present invention. In practice, the number of aspiration levels may be empirically determined for different types of sample liquids, like those seen in Table 1, as a function of the total amount of liquid 14 in container 16 or alternately as a function of the distance between the uppermost and lowermost levels of liquid 14 in container 16.

Under control of computer 15, transport mechanism 34 positions pipette 12 at an aspirating location above tube L and lowers pipette 12 into tube L to ascertain the uppermost level of fluid 14 therein. From the known location of the bottom of tube L, computer 15 is programmed to calculate the eight different depths at which eight constant volume partial aliquots of sample liquid 14 are to be aspirated into lumen 18 from tube L. Computer 15 then operates transport mechanism 34 to lower pipette 12 to the first of the eight different depths and controls piston assembly 24 so as to aspirate the desired partial aliquot of sample liquid 14 into lumen 18. This process is repeated at each of the remaining seven different depths to produce the desired full aliquot of sample liquid 14. If desired, computer 15 may operate transport mechanism 34 and piston assembly 24 to dispense a desired amount of sample liquid 14 from lumen 18 into an assay cuvette.

This same process may be employed for aspiration of liquid from tubes M and R, except that, as explained above, the eight different depths at which eight constant volume partial aliquots of sample liquid 14 are aspirated will be smaller and larger, respectively, than the depths at which sample liquid 14 is from tube L.

FIG. 3 illustrates an alternate embodiment of the present invention in an instance that three tubes L. M. and R contain different amounts of a liquid susceptible to sedimentation (the liquid is shaded more darkly at the bottom of the column of liquid than at the top) and it has been predetermined to employ equally spaced apart eight aspiration levels at which eight constant volume aspirations of partial aliquots are effected. In this instance, computer 15 operates transport mechanism 34 to lowers pipette 12 into tube L to ascertain the uppermost level of fluid 14 therein. From the known location of the bottom of tube L, computer 15 is programmed to determine the number of different depths at which constant volume partial aliquots of sample liquid 14 are to be aspirated into lumen 18 from tube L. In this illustration, for tube L it is possible to aspirate at eight different depths. Computer 15 then operates transport mechanism 34 to lower pipette 12 to the first of the eight equally spaced depths and controls piston assembly 24 so as to aspirate the desired partial aliquot of sample liquid 14 into lumen 18. This process is repeated at each of the remaining seven different depths to produce the desired full aliquot of sample liquid 14.

This same process may be employed for aspiration of liquid from tubes M and R, except that, as explained above, the number of different depths at which constant volume partial aliquots of sample liquid 14 may be aspirated will be smaller and larger, respectively, than the number of depths at which sample liquid 14 is from tube L.

Figure 4:
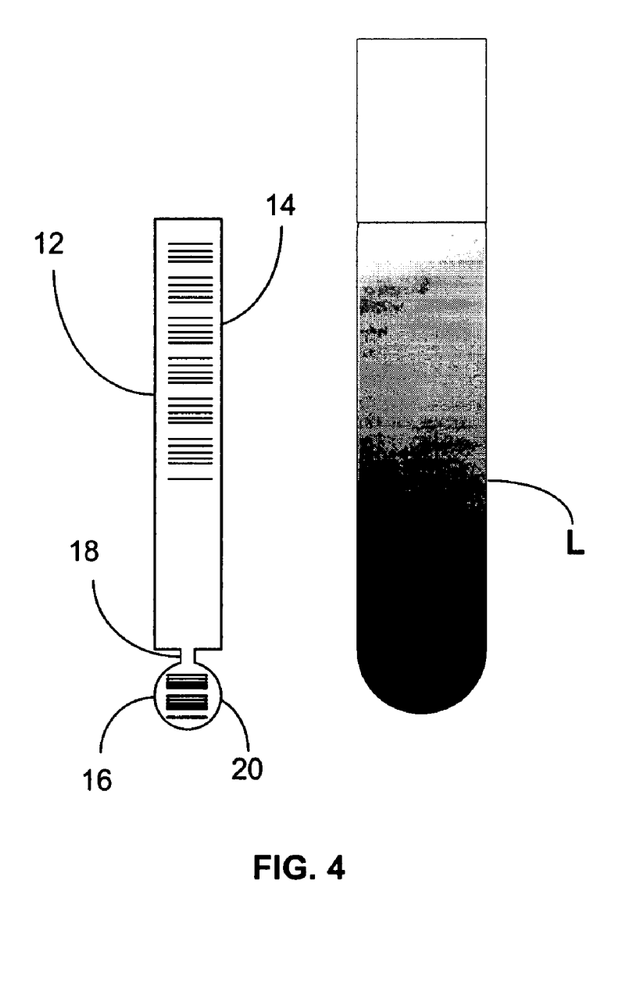
FIG. 4 illustrates a dual indicia bar code useful for identifying sample tubes like those seen in FIG. 1; and, FIGS. 4A and 4B illustrate the dual indicia bar code of FIG. 4 applied to a sample tubes like those seen in FIG. 1
Figure 4A:
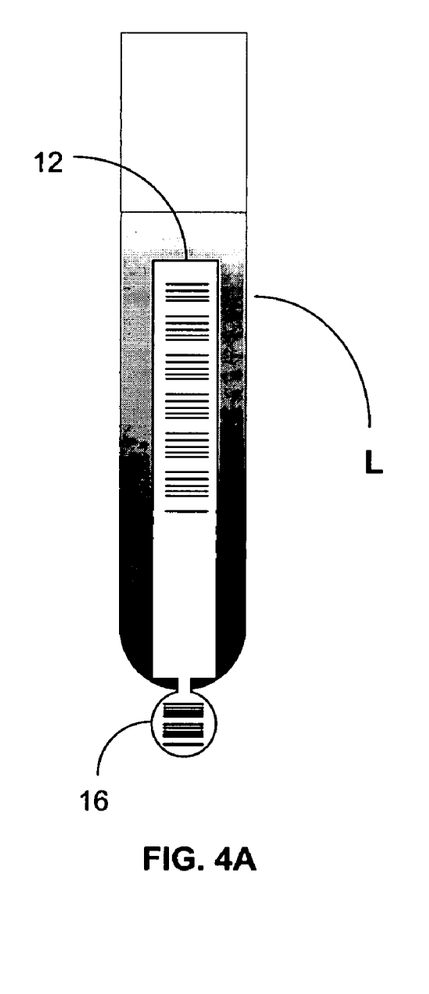
Figure 4B:
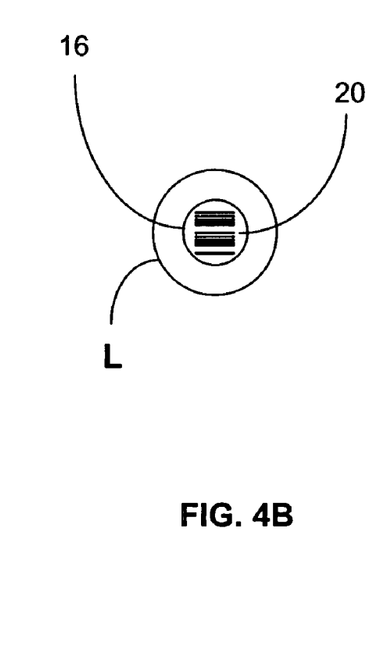

FIG. 4 illustrates a dual indicia bar code 12 useful for identifying sample tubes L, bar code 12 having a conventional bar code indicia 14 printed thereon. Bar code 12 further comprises a tab section 16 affixed thereto by means of a narrow extension 18, tab section 16 having a miniaturized bar code indicia 20 printed thereon. Both bar code indicia 14 and bar code indicia 20 are encoded so as to identify the contents of tube L. FIG. 4A illustrates the dual indicia bar code 12 of FIG. 4 applied to a sample tube L with bar code indicia 14 around the external side of tube L while FIG. 4B illustrates miniaturized bar code indicia 20 on the bottom of tube L. Bar code indicia 14 may be read using a conventional bar code reader as is often mounted on the operating plane of a clinical analyzer; bar code indicia 20 however may be read by a bar code reader located below operating plane of a clinical analyzer when tube L is carried in a slot in a tube rack, the slot having a hole in its bottom so that bar code indicia 20 is visible from beneath the rack.

Those skilled in the art will appreciate that the embodiments of the invention disclosed herein are illustrative of the principles of the invention and that other modifications may be employed which are still within the scope of the invention. For example, as may be seen by comparison of tubes L and M in FIG. 3, it may be desired to not aspirate a partial aliquot of sample liquid 14 at the uppermost level of fluid 14, as is shown for tube M but not for tube L. Similarly, it may be desired to aspirate or not aspirate a partial aliquot of sample liquid 14 at the lowermost level of fluid 14.

The method also could also be used to aspirate a variable volume partial aliquot of sample liquid 14, for example a larger amount at the middle range than at the uppermost and lowermost ranges. Accordingly, the present invention is not limited to those embodiments precisely shown and described in the specification but only by the following claims.

What is claimed is:

1. A method for controlling an aspiration process during which liquid having uppermost and lowermost levels is aspirated from a container into a pipette comprising the steps of:

(a) lowering an aspiration pipette a first depth into a liquid in a container, stopping and aspirating a known volume of liquid into the pipette;

(b) lowering said aspiration pipette an additional distance into the liquid, said additional distance being equal to the distance of said first depth, stopping and aspirating an additional volume of liquid into the pipette, said additional volume being equal to said known volume;

(c) repeating step (b) as required until said aspiration pipette is a predetermined distance from the bottom of the container.

2. The method of claim 1 wherein said first depth is determined by:

(a) ascertaining the uppermost level of liquid in said container;

(b) calculating the distance between the uppermost level of liquid and the bottom of the container; and, (c) dividing said calculated distance by an integer.

3. The method of claim 2 wherein said integer is determined by the amount of liquid in the container.

4. The method of claim 2 wherein said integer is a predetermined constant.

5. The method of claim 1 wherein the liquid has a composition that varies between the uppermost and lowermost levels of the liquid.

6. The method of claim 1 wherein the liquid is a sedimented liquid.

7. The method of claim 1 wherein the container has a side and a bottom, the container further having a bar code attached thereto, the bar code comprising a conventional bar code indicia and a tab section, the tab section having a miniaturized bar code indicia printed thereon.

8. The method of claim 7 wherein the conventional bar code indicia is attached to the side of the container and wherein the miniaturized bar code indicia is attached to the bottom of the container.

* * * * *

UNITED STATES PATENT AND TRADEMARK OFFICE
CERTIFICATE OF CORRECTION

PATENT NO.        : 7,205,158 B2                                       Page 1 of 1
APPLICATION NO.   : 10/871409
DATED             : April 17, 2007
INVENTOR(S)       : Pankratz et al.

It is certified that error appears in the above-identified patent and that said Letters Patent is hereby corrected as shown below:

On the title page in the left hand column, in the Inventors section (75); please add
-- William Kirk Hessler, Newark, DE (US) --

Signed and Sealed this

Tenth Day of November, 2009

David J. Kappos
*Director of the United States Patent and Trademark Office*